(12) United States Patent
Nagy et al.

(10) Patent No.: US 11,590,477 B2
(45) Date of Patent: Feb. 28, 2023

(54) TITANATED CATALYSTS, METHODS OF PREPARING TITANATED CATALYSTS, AND METHODS OF EPOXIDATION

(71) Applicant: Lyondell Chemical Technology, L.P., Houston, TX (US)

(72) Inventors: Sandor Nagy, Seabrook, TX (US); Nicholas Bruschi, Houston, TX (US); Elizabeth I. Ross-Medgaarden, Humble, TX (US); David W. Leyshon, Houston, TX (US); Barbara Kimmich, Houston, TX (US)

(73) Assignee: Lyondell Chemical Technology, L.P., Houston, TX (US)

( * ) Notice: Subject to any disclaimer, the term of this patent is extended or adjusted under 35 U.S.C. 154(b) by 208 days.

(21) Appl. No.: 17/087,165

(22) Filed: Nov. 2, 2020

(65) Prior Publication Data
US 2021/0129112 A1 May 6, 2021

Related U.S. Application Data

(60) Provisional application No. 62/930,281, filed on Nov. 4, 2019.

(51) Int. Cl.
*B01J 21/06* (2006.01)
*B01J 21/08* (2006.01)
*C08F 8/08* (2006.01)

(52) U.S. Cl.
CPC ............ *B01J 21/063* (2013.01); *B01J 21/08* (2013.01); *C08F 8/08* (2013.01)

(58) Field of Classification Search
CPC ...... B01J 21/063; B01J 21/08; B01J 37/0201; B01J 37/0203; B01J 37/0209; B01J 37/088; C08F 8/08; C07D 301/19
See application file for complete search history.

(56) References Cited

U.S. PATENT DOCUMENTS

| | | | |
|---|---|---|---|
| 5,759,945 A | 6/1998 | Carroll et al. | |
| 6,187,934 B1 | 2/2001 | Tsuji et al. | |
| 10,017,484 B2 | 7/2018 | Nagy et al. | |
| 2001/0025008 A1 | 9/2001 | Hu et al. | |
| 2015/0182959 A1 | 7/2015 | Nenu | |

FOREIGN PATENT DOCUMENTS

| | | |
|---|---|---|
| WO | 0072961 A1 | 12/2000 |
| WO | 2017080962 A1 | 5/2017 |

OTHER PUBLICATIONS

Translation of Corma Canos et al. (WO 00/44670), published Aug. 3, 2000.*
Haber, J. et al., 1995, Pure and Applied Chemistry, 67, 8/9, 1257-1306.*
The International Search Report and The Written Opinion for PCT/US2020/058558 dated Feb. 3, 2021.

* cited by examiner

*Primary Examiner* — Brian A McCaig

(57) ABSTRACT

Methods of preparing titanated silica catalysts, and titanated silica catalysts. The titanated silica catalysts may include a silica support, which may include spherical beads. Methods of olefin epoxidation, which may include contacting an olefin with a titanated silica catalyst in the presence of an oxidant.

18 Claims, 1 Drawing Sheet

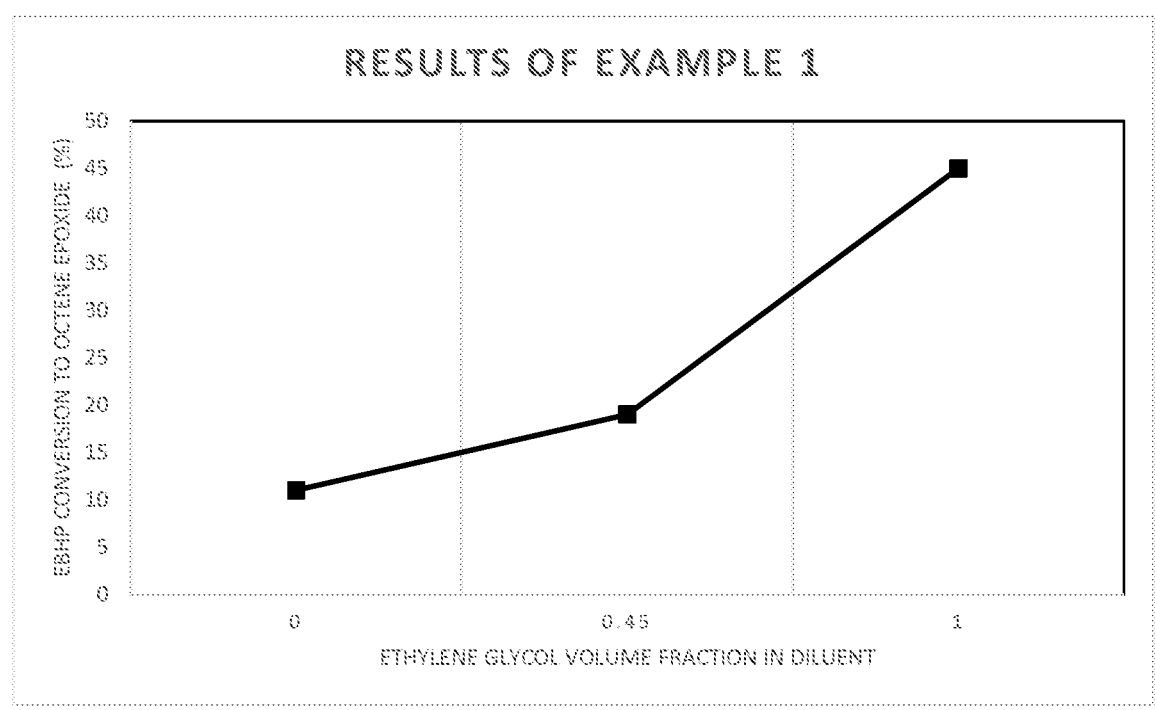

TITANATED CATALYSTS, METHODS OF PREPARING TITANATED CATALYSTS, AND METHODS OF EPOXIDATION

PRIOR RELATED APPLICATIONS

This application claims the benefit of priority to U.S. Provisional Application No. 62/930,281, filed Nov. 4, 2019, which is incorporated here by reference in its entirety.

BACKGROUND

Titanated silica systems are catalysts for propylene epoxidation processes that rely on hydroperoxides, such as t-butyl hydroperoxide (TBHP), 1-ethylbutyl hydroperoxide (EBHP), or cumene hydroperoxide (CHP). These processes include the treatment of silica supports with titanium chloride or one or more titanium alkoxides. Titanium alkoxides and titanium halides, however, may be moisture sensitive, pyrophoric, or a combination thereof. Although relatively inexpensive to purchase, titanium chloride may be moisture sensitive, corrosive, and toxic, thereby making it expensive to handle.

U.S. Patent Application Publication No. 2015/01822959, which is incorporated herein by reference, discloses a process for preparing a titanium catalyst system for epoxidation reactions that includes (i) impregnating a silica carrier with a liquid solution of a titanium compound in an inorganic solvent system, (ii) drying the carrier, (iii) calcinating (i.e., "calcining") the dried product, and (iv) silylating the calcinated (i.e., "calcined") product.

There remains a need for improved processes for preparing the foregoing catalysts, especially high-volume commercial catalysts, that are efficient, safer, cheaper, more environmentally friendly, or a combination thereof.

Many fixed bed epoxidation catalysts include titanated silica supports. The supports may have a weight average particle size of 0.2 mm to 3 mm, and may include unevenly shaped particles. An example of supports is disclosed at WO 2017/080962, which is incorporated herein by reference. The supports of WO 2017/080962 have a surface area of 330 $m^2/g$ to 450 $m^2/g$. These supports, however, may suffer from one or more disadvantages, such as a large delta pressure that may be associated with their use in fixed bed reactors.

There remains a need for catalyst supports, including titanated silica supports, that overcome one or more of these disadvantages, and/or perform better in fixed bed reactors.

BRIEF SUMMARY

Provided herein are methods of preparing titanated silica catalysts that are safe, relatively inexpensive, and/or environmentally friendly. The titanated silica catalysts can exhibit improved catalyst performance, such as in epoxidation processes, and the degree of improvement is surprising. Also provided herein are titanated silica catalysts and methods of preparing titanated silica catalysts that exhibit improved results in fixed bed reactors. For example, the titanated silica catalysts can exhibit a surprising reduction in delta pressure compared to other catalyst systems.

In one aspect, a method of preparing titanated silica catalysts is provided, the method comprising: providing a liquid comprising (i) a water soluble organic compound, and (ii) a water soluble titanium compound; contacting a silica support with the liquid to deposit at least a portion of the water-soluble titanium compound on the silica support to form a titanium-treated silica support; calcinating the titanium-treated silica support; and silylating the titanium-treated silica support to form the titanated silica catalyst.

In some embodiments, the methods include providing a liquid that includes (i) a water soluble organic compound, and (ii) a water soluble titanium compound; and contacting a silica support with the liquid to deposit at least a portion of the water soluble titanium compound on the silica support to form a titanium-treated silica support. The methods may also include calcinating the titanium-treated silica support, and/or silylating the titanium-treated silica support.

In some embodiments, the methods include providing a silica support that includes a plurality of spherical silica beads having an average diameter of about 0.1 mm to about 5 mm.

In some embodiments, the methods include providing a liquid that includes (i) a water soluble organic compound, and (ii) titanium (IV) bis(ammonium lactato) dihydroxide; and contacting a silica support with the liquid to deposit at least a portion of the titanium(IV) bis(ammonium lactato) dihydroxide on the silica support to form a titanium-treated silica support. The methods may also include calcinating the titanium-treated silica support, and/or silylating the titanium-treated silica support to form a titanated silica catalyst. The plurality of spherical silica beads also may have a surface area of about 400 $m^2/g$ to about 600 $m^2/g$, a pore volume of about 1 cc/g to about 2.5 cc/g, or a combination thereof. Textural properties are measured by nitrogen adsorption isotherms collected at 77 k in the region of P/P0<0.3 (BET surface area) and P/P0>0.95 (pore volume).

In another aspect, methods of olefin epoxidation are provided. In some embodiments, the methods include providing a titanated silica catalyst described herein or prepared by the methods described herein; and contacting an olefin with the titanated silica catalyst in the presence of an oxidant and in conditions effective to epoxidize the olefin to form an epoxidized olefin.

In yet another aspect, titanated catalysts are provided. In some embodiments, the titanated catalysts include a titanated catalyst system made according to any of the methods described herein.

Additional aspects will be set forth in part in the description which follows, and in part will be obvious from the description, or may be learned by practice of the aspects described herein. The advantages described herein will be realized and attained by means of the elements and combinations particularly pointed out in the appended claims. It is to be understood that both the foregoing general description and the following detailed description are exemplary and explanatory and are not restrictive.

BRIEF DESCRIPTION OF THE DRAWINGS

The FIGURE is a plot of epoxide conversion percentages achieved with three embodiments of liquids that include titanium(IV) bis(ammonium lactato)dihydroxide.

DETAILED DESCRIPTION

Provided herein are titanated silica catalysts, and methods of preparing titanated silica catalysts. The titanated catalysts provided herein may include a titanium-treated silica support. The titanium-treated silica support may include a plurality of spherical silica beads having (i) an average diameter of about 0.1 mm to about 5 mm, (ii) a surface area of about 400 $m^2/g$ to about 600 $m^2/g$, and (iii) a pore volume of about 1 cc/g to about 2.5 cc/g.

Methods of Preparing Titanated Silica Catalysts

Methods of preparing titanated silica catalysts are provided. In some embodiments, the methods provided herein include providing a liquid that includes (i) a water soluble organic compound, and (ii) titanium(IV) bis(ammonium lactato)dihydroxide; and contacting a silica support with the liquid to deposit at least a portion of the titanium(IV) bis(ammonium lactato)dihydroxide on the silica support to form a titanium-treated silica support. A material is "on the silica support" when it is deposited on and/or in any portion of the silica support, such as a surface, a pore, an internal area (e.g., interstitial space), etc.

The contacting of a silica support with a liquid may be achieved in any manner, including any technique. In some embodiments, the contacting of the silica support with the liquid includes impregnating the silica support with the liquid. A silica support is "impregnated" with a liquid when at least a portion of the liquid contacts a non-surface portion of the silica support. For example, impregnating a silica support with a liquid may result in the presence of at least a portion of the liquid in one or more internal spaces of the silica support.

In some embodiments, the impregnating of a silica support includes subjecting the silica support to an incipient wetness impregnation process. In some such embodiments, a vacuum-assisted incipient wetness impregnation process may be used. A vacuum-assisted incipient wetness impregnation process may rely at least in part on capillary action to impregnate a silica support with a liquid. In some embodiments, the methods provided herein include providing a silica support that includes a plurality of spherical silica beads having an average diameter of about 0.1 mm to about 5 mm; contacting the silica support with a water soluble organic compound, and titanium(IV) bis(ammonium lactato) dihydroxide to form a titanium-treated silica support. The method may also include calcinating the titanium-treated silica support to form a calcinated titanium-treated silica support; and silylating the calcinated titanium-treated silica support to form the titanated silica catalyst.

In some embodiments, the methods provided herein include calcinating a titanium-treated silica support; and silylating the titanium-treated silica support to form a titanated silica catalyst.

In some embodiments, the calcinating of the titanium-treated silica support includes subjecting the titanium-treated silica support to an elevated temperature of about 100° C. to about 1,000° C., about 300° C. to about 800° C., or about 600° C. to about 800° C. In some embodiments, the calcinating of a titanium-treated silica support includes heating the titanium-treated silica support in air to a temperature of about 500° C. to about 750° C. for about 1 hour to about 3 hours. In some embodiments, a temperature gradient is used. In some embodiments, a titanium-treated silica support is heated to about 100° C. for about 15 minutes, then to about 250° C. for about 15 minutes, and then to about 700° C. for about 2 hours. In some embodiments, the calcination is performed under an inert atmosphere, such as nitrogen or a noble gas. In some embodiments, at least a first portion of the calcination is performed under an inert gas, and then at least a second portion of the calcination is performed in air. In some embodiments, the calcination is carried out in an atmosphere which includes oxygen. In some embodiments, the calcination is carried out in the absence of oxygen.

Optionally, after the calcinating of a titanium-treated silica support, the calcinated titanium-treated silica support may be washed.

In some embodiments, a titanium-treated silica support is washed with a solvent. In some embodiments, the solvent is a hydroxyl containing liquid. In some embodiments, the hydroxyl containing liquid includes an alcohol, water, or a combination thereof. The alcohol may include a $C_1$-$C_{18}$ hydrocarbyl substituted with at least one hydroxyl moiety. In some embodiments, a titanium-treated silica support is washed with a hydroxyl containing liquid at ambient temperature.

A washed titanium-treated silica support may be dried. In some embodiments, the drying includes subjecting the washed titanium-treated silica support to an elevated temperature. In some embodiments, the temperature is greater than 50° C. In some embodiments, the temperature is about 50° C. to about 200° C. In some embodiments, the temperature is about 100° C. to about 150° C. In some embodiments, the washed titanium-treated silica support is dried under a stream of an inert gas. In some embodiments, the washed titanium-treated silica support is dried for a time of about 0.1 hours to about 2 hours. In some embodiments, the washed titanium-treated silica support is dried for a time of about 1 hour to about 4 hours. In some embodiments, the time is about 2 hours.

In some embodiments, the silylating of the titanium-treated silica support includes contacting the titanium-treated silica support with a silylating agent. Any silylating agent may be used. In some embodiments, the silylating agent is an organosilane, an organosilylamine, an organosilazane, or a combination thereof. Examples of silylating agents are disclosed at U.S. Pat. No. 10,017,484, which is incorporated herein by reference.

In some embodiments, silylating agent is an organodisilazane of the following formula:

$R_3SiNHSiR'_3$, wherein each R and R' is independently selected from a $C_1$-$C_6$ hydrocarbyl. In some embodiments, the silylating agent includes hexamethyldisilazane.

Silica Support

Any silica support may be used in the methods provided herein. Non-limiting examples of silica supports include those disclosed at U.S. Pat. No. 10,017,484, which is incorporated herein by reference.

In some embodiments, the silica support includes an inorganic siliceous solid, such as silicon oxide. In some embodiments, the siliceous solid is an amorphous silicon oxide. In some embodiments, the silica support is porous. A silica support is porous when it includes one or more pores and/or interstices within its structure.

In some embodiments, the silica support includes a plurality of spherical silica beads, tablets, extrudates and particulates. A bead is "spherical" when [1] it is spherical, [2] its smallest diameter is equal to or greater than 95% of its largest diameter (e.g., a smallest diameter of at least 1.9 mm and a largest diameter of 2 mm), and/or [3] it would satisfy element [1] and/or [2], but for an imperfection, such as a surface imperfection (e.g, trench, depression, etc.). Non-limiting examples of spherical silica beads include Alpha-Cat® 4000 silica beads available from PQ Corporation (Malvern, Pa., USA).

In some embodiments, the silica support of the catalyst includes silicon oxide. In some embodiments, the silica support includes silicon oxide and titanium oxide. In some embodiments, the silica support includes at least 90% by weight of silicon oxide, based on the weight of the silica support. In some embodiments, the silica support includes at least 95% by weight of silicon oxide, based on the weight of the silica support. The percentage of silicon oxide and one or more other oxides in the silica support may be measured using XRF (x-ray fluorescence spectroscopy). In some embodiments, the one or more other oxides, such as titanium oxide, account for less than about 10% by weight of the silica support, based on the weight of the silica support. In some embodiments, the one or more other oxides account for about 0.01% by weight to about 9.9% by weight of the silica support, based on the weight of the silica support.

In some embodiments, the silicon oxide includes silicon oxide that is flocculated and/or otherwise linked together to form densely packed masses of silica oxide. In some embodiments, the silicon oxide includes synthetic silica powder. The synthetic silica powder may be a powder that is flocculated into open-packed, easily disintegrated, and/or loosely knit aggregates.

In some embodiments, the silica support includes silica-alumina, silica-magnesia, silica-zirconia, silica-alumina-boria, silica-aluminum-magnesia, or a combination thereof. In some embodiments, the silica support includes a plurality of molecular sieves. The plurality of molecular sieves may include large pore and/or mesoporous molecular sieves, such as MCM-41, MCM-48, M41S, or a combination thereof.

In some embodiments, the silica support has a surface area of about 300 $m^2/g$ to about 700 $m^2/g$. Textural properties are measured by nitrogen adsorption isotherms collected at 77 k in the region of P/P0<0.3 (BET surface area) and P/P0>0.95 (pore volume). In some embodiments, the silica support has a surface area of about 400 $m^2/g$ to about 600 $m^2/g$. In some embodiments, the silica support has a surface area of about 450 $m^2/g$ to about 550 $m^2/g$. In some embodiments, the silica support has a surface area of about 400 $m^2/g$ to about 600 $m^2/g$, and the silica support includes a plurality of spherical silica beads. In some embodiments, the silica support has a surface area of about 450 $m^2/g$ to about 550 $m^2/g$, and the silica support includes a plurality of spherical silica beads. In some embodiments, the silica support has a surface area of about 450 $m^2/g$ to about 460 $m^2/g$. In some embodiments, the silica support has a surface area of about 530 $m^2/g$ to about 540 $m^2/g$.

In some embodiments, the silica support has a relatively high surface area, e.g., greater than 800 $m^2/g$. In some embodiments, the surface area of the silica support is about 800 $m^2/g$ to about 1200 $m^2/g$. In some embodiments, the surface area of the silica support is about 900 $m^2/g$ to about 1100 $m^2/g$. In some embodiments, the surface area of the silica support is about 910 $m^2/g$ to about 970 $m^2/g$. In some embodiments, the surface area of the silica support is about 950 $m^2/g$. In some embodiments, the surface area of the silica support is greater than 1000 $m^2/g$.

In some embodiments, the silica support has a pore volume of about 1 $g/cm^3$ to about 3 $g/cm^3$. In some embodiments, the silica support has a pore volume of about 1 $g/cm^3$ to about 2.5 $g/cm^3$. In some embodiments, the silica support has a pore volume of about 1 $g/cm^3$ to about 1.5 $g/cm^3$. In some embodiments, the silica support has a pore volume of about 1 $g/cm^3$ to about 2.5 $g/cm^3$, and the silica support includes a plurality of spherical silica beads.

In some embodiments, the silica support has a relatively high pore volume, e.g., greater than 1.25 $g/cm^3$. In some embodiments, the pore volume of the silica support is about 1.25 $g/cm^3$ to about 3.50 $g/cm^3$. In some embodiments, the pore volume of the silica support is about 1.5 $g/cm^3$ to about 3.0 $g/cm^3$. In some embodiments, the pore volume of the silica support is about 2.0 $g/cm^3$ to about 2.5 $g/cm^3$. In some embodiments, the pore volume of the silica support is about 2.20 $g/cm^3$ to about 2.5 $g/cm^3$. In some embodiments, the pore volume of the silica support is greater than 2.0 $g/cm^3$. The pore volume and/or surface area of a silica support may be measured using nitrogen porosimetry.

In some embodiments, the silica support has an average pore diameter greater than 70 Å. In some embodiments, the average pore diameter of the silica support is about 70 Å to about 150 Å. In some embodiments, the average pore diameter of the silica support is about 90 Å to about 110 Å. In some embodiments, the average pore diameter of the silica support is about 91 Å to about 108 Å.

In some embodiments, the silica support has a high surface area and a high pore volume, e.g., a surface area greater than 800 $g/cm^3$ and a high pore volume greater than 1.25 $g/cm^3$.

The silica support may have any desired particle size. In some embodiments, a desired particle size of the silica support is obtained through crushing and/or extruding. In some embodiments, a desired particle size of the silica support is obtained by classifying the silica support through a sieve. In some embodiments, the average diameter of the silica support is less than 5.0 mm. In some embodiments, the average diameter of the silica support is about 0.1 mm to about 5.0 mm. In some embodiments, the average diameter of the silica support is about 0.2 mm to about 4 mm. In some embodiments, the silica support includes a plurality of spherical silica beads having an average diameter of about 0.5 mm to about 3 mm. In some embodiments, the silica support includes a plurality of spherical silica beads having an average diameter of from about 0.3 mm to about 2 mm. In some embodiments, the silica support includes a plurality of spherical silica beads having an average diameter of from about 0.4 mm to about 4 mm. In some embodiments, the silica support includes a plurality of spherical silica beads having an average diameter of from about 0.5 mm to about 4 mm.

In some embodiments, the silica support is dried before the silica support is contacted with a liquid. In some embodiments, the drying of the silica support includes heating the silica support to a temperature of about 100° C. to about 850° C. In some embodiments, the temperature is greater than 120° C. In some embodiments, the temperature is about 150° C. to about 300° C. In some embodiments, the silica support is dried in a vacuum. In some embodiments, the silica support is dried under a flowing stream of an inter gas, such as nitrogen or a noble gas. In some embodiments, the silica support is dried for a time of about 1 hour to about 48 hours. In some embodiments, the silica support is dried for a time of about 2 hours to 24 hours.

A water soluble organic compound may be adsorbed to a silica support. In some embodiments, the silica support includes less than 3% by weight of carbon, based on the weight of the silica support. In some embodiments, the silica support includes about 0.05% by weight to about 3% by weight of carbon, based on the weight of the silica support. In some embodiments, the silica support includes about 1% by weight to about 2% by weight of carbon from an adsorbed water soluble organic compound and/or other materials. In some embodiments, the carbon content of the silica support is measured using carbon nitrogen analysis by converting the carbon into carbon dioxide at a high temperature.

Titanium(IV) Bis(Ammonium Lactato)Dihydroxide

In some embodiments, the methods described herein include providing a liquid that includes titanium(IV) bis (ammonium lactato)dihydroxide, which may have the following structure:

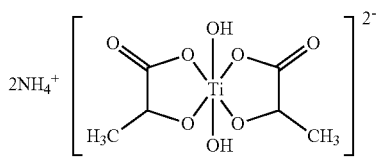

In some embodiments, titanium(IV) bis(ammonium lactato)dihydroxide is present in a liquid at an amount of about 5% to about 70% by weight, based on the weight of the liquid. In some embodiments, titanium(IV) bis(ammonium lactato)dihydroxide is present in a liquid at an amount of about 30% to about 70% by weight, based on the weight of the liquid. In some embodiments, titanium(IV) bis(ammonium lactato)dihydroxide is present in a liquid at an amount of about 40% to about 60% by weight, based on the weight of the liquid. In some embodiments, titanium(IV) bis(ammonium lactato)dihydroxide is present in a liquid at an amount of about 50% by weight, based on the weight of the liquid.

Water Soluble Organic Compound

As used herein, the phrase "water soluble organic compound" refers to any compound that includes at least one carbon atom, and has a solubility in water of at least 900 mg/L, or, in some embodiments, at least 1,000 mg/L. In some embodiments, the "water soluble organic compound" is a liquid at room temperature and pressure.

In some embodiments, the water soluble organic compound includes a $C_1$-$C_4$ hydrocarbyl and at least one functional group that imparts water solubility or increases the water solubility of the $C_1$-$C_4$ hydrocarbyl. In some embodiments, the water soluble organic compounds includes a $C_1$-$C_4$ hydrocarbyl and at least one functional group selected from the group consisting of a hydroxyl, an amine, a carboxylic acid, an ester, an ether, a ketone, and an aldehyde. For example, the $C_1$-$C_4$ hydrocarbyl may be bonded to [1] a hydroxyl functional group, [2] two hydroxyl functional groups, [3] a hydroxyl functional group and an amine functional groups, [4] an amine functional group, [5] two amine functional groups, etc.

A $C_1$-$C_4$ hydrocarbyl may be bonded to at least one functional group that imparts water solubility or increases the water solubility of the $C_1$-$C_4$ hydrocarbyl (e.g., substituted with a hydroxyl functional group). The at least one functional group that imparts water solubility or increases the water solubility of the $C_1$-$C_4$ hydrocarbyl may be bonded to at least two carbon atoms of the $C_1$-$C_4$ hydrocarbyl (e.g., an ether functional group bonded to two carbon atoms). In some embodiments, a $C_1$-$C_4$ hydrocarbyl is substituted with a first functional group that imparts water solubility or increases the water solubility of the $C_1$-$C_4$ hydrocarbyl, and a second functional group that imparts water solubility or increases the water solubility of the $C_1$-$C_4$ hydrocarbyl.

The phrase "$C_1$-$C_{30}$ hydrocarbyl", "$C_1$-$C_4$ hydrocarbyl", "$C_2$ hydrocarbyl", and the like, as used herein, refer to aliphatic groups containing 1 to 30 carbon atoms, 1 to 4 carbon atoms, or 1 carbon atom, respectively. Examples of aliphatic groups, in each instance, include, but are not limited to, an alkyl group, a cycloalkyl group, an alkenyl group, a cycloalkenyl group, an alkynyl group, an alkadienyl group, a cyclic group, and the like, and includes substituted, unsubstituted, branched, and linear analogs or derivatives thereof, in each instance having 1 to 30 carbon atoms, 1 to 4 carbon atoms, 1 carbon atom, etc. Examples of alkyl groups include, but are not limited to, methyl, ethyl, propyl, isopropyl, n-butyl, t-butyl, and isobutyl. Cycloalkyl moieties may include cyclopropyl and cyclobutyl. Representative alkenyl moieties include vinyl, allyl, 1-butenyl, 2-butenyl, and isobutylenyl. Representative alkynyl moieties include acetylenyl, propynyl, 1-butynyl, and 2-butynyl.

In some embodiments, the water soluble organic compound includes ethylene glycol, methanol, ethanol, or a combination thereof.

Unless otherwise indicated, the term "substituted," when used to describe a chemical structure or moiety, refers to a derivative of that structure or moiety wherein one or more of its hydrogen atoms is substituted with a chemical moiety or functional group such as a hydroxyl, alkoxy, alkanoyloxy, alkoxycarbonyl, alkenyl, alkyl (e.g., methyl, ethyl, etc.), alkynyl, alkylcarbonyloxy (—OC(O)alkyl), amide (—C(O)NH-alkyl- or -alkylNHC(O)alkyl), tertiary amine (such as alkylamino, arylamino, arylalkylamino), azo, carbamoyl (—NHC(O)O-alkyl- or —OC(O)NH-alkyl), carbamyl (e.g., $CONH_2$, as well as CONH-alkyl, CONH-aryl, and CONH-arylalkyl), carboxyl, carboxylic acid, cyano, ester, ether (e.g., methoxy, ethoxy), halo, haloalkyl (e.g., —$CCl_3$, —$CF_3$, —$C(CF_3)_3$), heteroalkyl, isocyanate, isothiocyanate, nitrile, nitro, phosphodiester, sulfide, sulfonamido (e.g., $SO_2NH_2$, $SO_2NR'R''$), sulfone, sulfonyl (including alkylsulfonyl, arylsulfonyl and arylalkylsulfonyl), sulfoxide, thiol (e.g., sulfhydryl, thioether) or urea (—NHCONH-alkyl-).

Methods of Epoxidation

The catalysts described herein may be used in the production of epoxides from an olefin. Therefore, provided herein are methods of olefin epoxidation. The methods may include contacting an olefin with a titanated silica catalyst, as described herein, in the presence of an oxidant and in conditions effective to epoxidize the olefin to form an epoxidized olefin.

The methods of epoxidation described herein may include batch epoxidation methods, or continuous expoxidation methods.

In some embodiments, the catalysts described herein result in relatively higher conversion of an olefin into a product. In some embodiments, at least about 35 mol % of an olefin is converted to an epoxidized olefin in the methods of epoxidation described herein. In some embodiments, at least about 45 mol % of an olefin is converted to an epoxidized olefin in the methods of epoxidation described herein. In some embodiments, at least about 50 mol % of an olefin is converted to an epoxidized olefin in the methods of epoxidation described herein. In some embodiments, at least about 55 mol % of an olefin is converted to an epoxidized olefin in the methods of epoxidation described herein. In some embodiments, at least about 65 mol % of an olefin is converted to an epoxidized olefin in the methods of epoxidation described herein. In some embodiments, at least about 75 mol % of an olefin is converted to an epoxidized olefin in the methods of epoxidation described herein. In some embodiments, at least about 85 mol % of an olefin is converted to an epoxidized olefin in the methods of epoxidation described herein.

Any oxidant, i.e., oxidizing agent, may be used in the methods described herein. In some embodiments, the oxidizing agent is a hydroperoxide. In some embodiments, the hydroperoxide is an alkylhydroperoxide. In some embodiments, the alkyl group has from 1 to about 12 carbon atoms. In some embodiments, the alkyl group is tert-butyl. In other embodiments, the hydroperoxide is an aralkylhydroperoxide. In some embodiments, the aralkyl group has from 1 to about 24 carbon atoms. In some embodiments, the aralkyl group has from about 1 to about 12 carbon atoms. In some embodiments, the aralkyl group is ethylbenzyl or cumyl.

In some embodiments, the oxidizing agent is an organic hydroperoxide, such as tert-butyl hydroperoxide (TBHP), cumene hydroperoxide (CHP), ethylbenzene hydroperoxide, or 1-ethylbutyl hydroperoxide (EBHP).

Any olefin may be used in the methods of epoxidation described herein. As used herein, the term "olefin" may refer to any hydrocarbyl, such as a $C_1$-$C_{30}$ hydrocarbyl, that includes at least one non-aromatic double bond. In some embodiments, the olefin has 1 to 24 carbon atoms. In some embodiments, the olefin has 1 to 12 carbon atoms. In some embodiments, the olefin is propylene, 1-octene, or a combination thereof. In some embodiments, the olefin is substituted with one or more other functional groups, such as a hydroxyl or halide.

Any ratio of olefin to oxidant may be used in the methods of epoxidation described herein. In some embodiments, the molar ratio of olefin to oxidizing agent is from about 1:1 to about 20:1, or about 10:1 to about 12:1.

In some embodiments, at least a portion of an epoxidation reaction occurs in the liquid phase. In some embodiments, the liquid phase includes one or more liquids (e.g., one or more solvents) or inert diluents. In some embodiments, the liquid is a hydrocarbon precursor of the hydroperoxide (e.g., either a corresponding alkane or alcohol). If, for example, the hydroperoxide, in some embodiments, is tert-butyl hydroperoxide, then the liquid that may be optionally used may be tert-butanol.

The methods of epoxidation described herein may be modified by adjusting the pressure and/or the temperature. In some embodiments, the methods of epoxidation are carried out, at least in part, at a temperature from about 25° C. to about 200° C. In some embodiments, the temperature is from about 50° C. to about 160° C. In some embodiments, the temperature is from about 70° C. to about 140° C. In some embodiments, the methods of epoxidation are carried out, at least in part, at a pressure that is from about ambient pressure to greater than atmospheric pressure. In some embodiments, the pressure is from about 20 psi to about 1500 psi. In some embodiments, propylene used as the olefin, and the pressure is from about 400 psi to about 1000 psi.

In some embodiments, the epoxidation reaction includes multiple phases. For example, at least a portion of the reactants may be in a gaseous phase, and/or at least a portion of the reactants may be in a liquid phase, and/or at least a portion of the catalyst may be in a solid phase. In some embodiments, both reactants are in the liquid phase, and the catalyst is in the solid phase, such that the catalyst in the reaction mixture is used heterogeneously.

In some embodiments, the methods of epoxidation are performed in any commercially useful reactor. In some embodiments, the reactor is selected from a continuous or batch process reactor. Non-limiting examples of reactors include a fixed bed or a slurry reactor. When any of these reactors are used, the reaction may also include separating the reactants and catalyst from the products. In some embodiments, the methods of epoxidation include a fractional distillation, a selective extraction, filtration, and/or a similar separation technique. In some embodiments, at least a portion of any unreacted reactants, a liquid, and/or a catalyst is reused in the epoxidation reaction.

The terms "a," "an," and "the" are intended to include plural alternatives, e.g., at least one. For instance, the disclosure of "a silica support," "an olefin," and the like, is meant to encompass one, or mixtures or combinations of more than one silica support, olefin, and the like, unless otherwise specified.

In the descriptions provided herein, the terms "includes," "is," "containing," "having," and "comprises" are used in an open-ended fashion, and thus should be interpreted to mean "including, but not limited to." When methods or systems are claimed or described in terms of "comprising" various components or steps, the methods or systems can also "consist essentially of" or "consist of" the various components or steps, unless stated otherwise.

Various numerical ranges may be disclosed herein. When Applicant discloses or claims a range of any type, Applicant's intent is to disclose or claim individually each possible number that such a range could reasonably encompass, including end points of the range as well as any sub-ranges and combinations of sub-ranges encompassed therein, unless otherwise specified. Moreover, numerical end points of ranges disclosed herein are approximate. As a representative example, Applicant discloses, in one embodiment, that a plurality of spherical silica beads has a pore volume of about 1 cc/g to about 2.5 cc/g. This range should be interpreted as encompassing values in a range of about 1 cc/g to about 2.5 cc/g, and further encompasses "about" each of 1.1 cc/g, 1.2 cc/g, 1.3 cc/g, 1.4 cc/g, 1.5 cc/g, 1.6 cc/g, 1.7 cc/g, 1.8 cc/g, 1.9 cc/g, 2 cc/g, 2.1 cc/g, 2.2 cc/g, 2.3 cc/g, and 2.4 cc/g, including any ranges and sub-ranges between any of these values.

Throughout this application, the term "about" is used to indicate that a value includes a variation of error, such as for the device, the method being employed to determine the value, or the variation that exists among the study subjects. The term "about" is used to imply the natural variation of conditions and represent a variation of plus or minus 5% of a value. In some embodiments, the variation is plus or minus 1% of a value.

The processes described herein may be carried out or performed in any order as desired in various implementations. Additionally, in certain implementations, at least a portion of the processes may be carried out in parallel. Furthermore, in certain implementations, less than or more than the processes described may be performed.

Many modifications and other implementations of the disclosure set forth herein will be apparent having the benefit of the teachings presented in the foregoing descriptions and the associated drawings. Therefore, it is to be understood that the disclosure is not to be limited to the specific implementations disclosed and that modifications and other implementations are intended to be included within the scope of the appended claims Examples The present disclosure is further illustrated by the following examples, which are not to be construed in any way as imposing limitations upon the scope thereof. On the contrary, it is to be understood that resort may be had to various other aspects, embodiments, modifications, and equivalents thereof which, after reading the description herein, may suggest themselves to one of ordinary skill in the art without departing from the spirit of the present disclosure or the scope of the appended claims. Thus, other aspects will be apparent to those skilled in the art from consideration of the specification and practice of the subject matter disclosed herein.

Example 1—Epoxidation Performance of Titanated Silica Catalysts

In this example, a silica support (AlphaCat® 4000, PQ Corporation, USA) was impregnated with three different liquids that included titanium(IV) bis(ammonium lactato) dihydroxide. The impregnation was achieved with an incipient wetness technique, and the impregnated silica support was calcined in air at 700° C. for 2 hours, and silylated with hexamethyldisilazane (HMDS) at 200° C.

Each of the three liquids included 50% by weight of the titanium(IV) bis(ammonium lactato)dihydroxide, based on the weight of each liquid. The first liquid included water and the titanium(IV) bis(ammonium lactato)dihydroxide. The second liquid included water, ethylene glycol, and titanium (IV) bis(ammonium lactato)dihydroxide. The third liquid included ethylene glycol and titanium(IV) bis(ammonium lactato)dihydroxide.

The performance of each of the titanated silica catalysts prepared with the three liquids of this example was tested in an octene/1-ethylbutyl hydroperoxide epoxidation process. The results of these tests are depicted at the following table:

TABLE 1

Results of Example 1

| Diluent Used in Liquid Containing 50% by weight of titanium(IV) bis(ammonium lactato)dihydroxide | Ethylene Glycol Volume Fraction in Diluent | 1-Ethylbutyl hydroperoxide conversion to Octene Epoxide (%) |
|---|---|---|
| Water | 0 | 11 |
| Water and Ethylene Glycol | 0.45 | 19 |
| Ethylene Glycol | 1 | 45 |

These results indicated that the third liquid, which included ethylene glycol and titanium(IV) bis(ammonium lactato)dihydroxide surprisingly outperformed the first and second liquids, which included water.

A plot of the results of Table 1 is provided at the FIGURE.

Three grams of the catalyst from Example 1 (where the diluent contained only ethylene glycol (no water)) was put into a 0.62" ID reactor with an oil jacket for heating. This catalyst was prepared by impregnation of 2.1 mm silica spheres as described above. The feed to the reactor was 50 gram/hour of pure propylene and 150 gram/hour of caustic washed and dried 1-ethylbutyl hydroperoxide (EBHP) oxidate containing about 9 wt % EBHP and about 88% ethylbenzene, the remainder being methyl benzyl alcohol and acetophenone. The pressure of the reactor was about 800 psig. After 100 hours on stream, the catalyst temperature necessary to convert 50% of the EBHP in the first reactor was 190 F. The effluent from the first reactor described above was sent to a second reactor containing 6 grams of the same catalyst and the temperature of the second reactor was adjusted to convert the remaining EBHP. The molar selectivity of propylene oxide with respect to EBHP converted in both reactors was 95.7%.

What is claimed is:

1. A method of preparing a titanated silica catalyst, the method comprising:
    providing a liquid comprising (i) a water soluble organic compound, and (ii) a water soluble titanium compound, wherein the water soluble titanium compound is titanium(IV) bis(ammonium lactato)dihydroxide; and
    contacting a silica support with the liquid to deposit at least a portion of the water soluble titanium compound on the silica support to form a titanium-treated silica support.

2. The method of claim 1, wherein in the water soluble organic compound is a mono or poly hydroxy alcohol.

3. The method of claim 1, wherein the water soluble organic compound comprises ethylene glycol or propylene glycol.

4. The method of claim 1, wherein the water soluble organic compound comprises methanol, ethanol, or a combination thereof.

5. The method of claim 1, wherein the titanium(IV) bis(ammonium lactato)dihydroxide is present in the liquid at an amount of from about 5% to about 70% by weight, based on the weight of the liquid.

6. The method of claim 1, wherein the titanium(IV) bis(ammonium lactato)dihydroxide is present in the liquid at an amount of about 40% to about 60% by weight, based on the weight of the liquid.

7. The method of claim 1, wherein the contacting of the silica support with the liquid comprises impregnating the silica support with the liquid.

8. The method of claim 7, wherein the impregnating of the silica support comprises subjecting the silica support to an incipient wetness impregnation process.

9. The method of claim 1, further comprising:
    calcinating the titanium-treated silica support; and
    silylating the titanium-treated silica support to form the titanated silica catalyst.

10. The method of claim 9, wherein the calcinating of the titanium-treated silica support comprises heating the titanium-treated silica support in air to a temperature of about 300° C. to about 800° C. for about 1 hour to about 3 hours.

11. The method of claim 9, wherein the silylating of the calcinated titanium-treated silica support comprises contacting the calcinated titanium-treated silica support with an organodisilazane of the following formula:

R$_3$SiNHSiR'$_3$, wherein each R and R' is independently selected from a monovalent C$_1$-C$_6$ hydrocarbyl.

12. The method of claim 11, wherein the silylating agent comprises hexamethyldisilazane.

13. A method of olefin epoxidation, the method comprising:
    providing the titanated silica catalyst prepared according to the method of claim 9; and
    contacting an olefin with the titanated silica catalyst in the presence of an oxidant and in conditions effective to epoxidize the olefin to form an epoxidized olefin.

14. The method of claim 13, wherein the olefin comprises propylene.

15. The method of claim 13, wherein the oxidant comprises a hydroperoxide.

16. The method of claim 15, wherein the oxidant comprises 1-ethylbutyl hydroperoxide (EBHP), t-butyl hydroperoxide (TBHP), or cumene hydrogen peroxide (CHP).

17. The method of claim 13, wherein about 20 mol % to 100 mol % of the olefin is converted to the epoxidized olefin.

18. The method of claim 13, wherein about 85 mol % to 100 mol % of the olefin is converted to the epoxidized olefin.

* * * * *